(12) United States Patent
Patton

(10) Patent No.: US 10,709,613 B1
(45) Date of Patent: Jul. 14, 2020

(54) PROTECTIVE COVER FOR CAST

(71) Applicant: Ingrid Patton, Tulsa, OK (US)

(72) Inventor: Ingrid Patton, Tulsa, OK (US)

( * ) Notice: Subject to any disclaimer, the term of this patent is extended or adjusted under 35 U.S.C. 154(b) by 429 days.

(21) Appl. No.: 15/431,825

(22) Filed: Feb. 14, 2017

Related U.S. Application Data

(60) Provisional application No. 62/333,444, filed on May 9, 2016.

(51) Int. Cl.
*A61F 13/04* (2006.01)
*A61F 5/01* (2006.01)
*A61F 15/00* (2006.01)

(52) U.S. Cl.
CPC .............. *A61F 13/043* (2013.01); *A61F 5/01* (2013.01); *A61F 13/041* (2013.01); *A61F 15/004* (2013.01)

(58) Field of Classification Search
CPC ..... A61F 13/041; A61F 13/043; A61F 15/004
USPC .............................................................. 602/3
See application file for complete search history.

(56) References Cited

U.S. PATENT DOCUMENTS

| | | | |
|---|---|---|---|
| 3,329,144 A * | 7/1967 | Liman ................... | A61F 15/004 602/3 |
| 3,416,518 A | 12/1968 | Samuels et al. | |
| 3,741,203 A * | 6/1973 | Liman ................... | A61F 15/004 602/3 |
| 3,810,466 A | 5/1974 | Rogers | |
| 5,682,616 A | 11/1997 | Pisano | |
| 6,047,403 A | 4/2000 | Juozaitis | |
| 6,512,158 B1 * | 1/2003 | Dobos ................... | A61F 15/004 602/3 |
| 6,892,733 B2 * | 5/2005 | Clinton ................. | A61F 5/0109 128/878 |
| 7,066,899 B2 | 6/2006 | Baron | |
| 7,314,457 B2 | 1/2008 | Reaux | |
| 7,762,968 B1 | 7/2010 | Hewitt | |
| 8,043,240 B2 | 10/2011 | Piatek | |
| 8,516,613 B2 * | 8/2013 | Crites ...................... | A41B 1/00 2/69 |
| 2001/0041853 A1 | 11/2001 | South et al. | |
| 2003/0191419 A1 | 10/2003 | Melin et al. | |
| 2003/0191424 A1 * | 10/2003 | Skinner ................. | A61F 15/004 602/62 |
| 2006/0224094 A1 | 10/2006 | Baron | |
| 2006/0253055 A1 | 11/2006 | Lindbery | |
| 2006/0276733 A1 * | 12/2006 | Evans .................... | A61F 15/004 602/3 |
| 2006/0287623 A1 | 12/2006 | Beck et al. | |
| 2009/0187126 A1 * | 7/2009 | Nelson .................. | A61F 15/004 602/3 |

(Continued)

*Primary Examiner* — Keri J Nelson
(74) *Attorney, Agent, or Firm* — Margaret Millikin

(57) ABSTRACT

A protective cover for use over a cast to prevent soiling of the cast from bodily fluids, excrement, etc. The cover remains on the cast until the cast is removed, but can be removed and replaced as needed. The protective cover is cleaned by wiping with a damp cloth or a disinfecting or soap wipe or solution. The material is soft and smooth to the skin and is hypoallergenic. The cover is in the shape of the cast with additional material provided at each of the cast openings so that the additional material can be tucked inside the cast. Depending on the shape of the cast, the cover may optionally be provided with a slit in the material to facilitate fitting it onto the cast. The slit is provided with fasteners on each side of the slit for securing the slit together to fit the cover over the cast.

17 Claims, 9 Drawing Sheets

(56) References Cited

U.S. PATENT DOCUMENTS

2010/0234781 A1  9/2010 Cassidy
2011/0282254 A1  11/2011 Gadlage

* cited by examiner

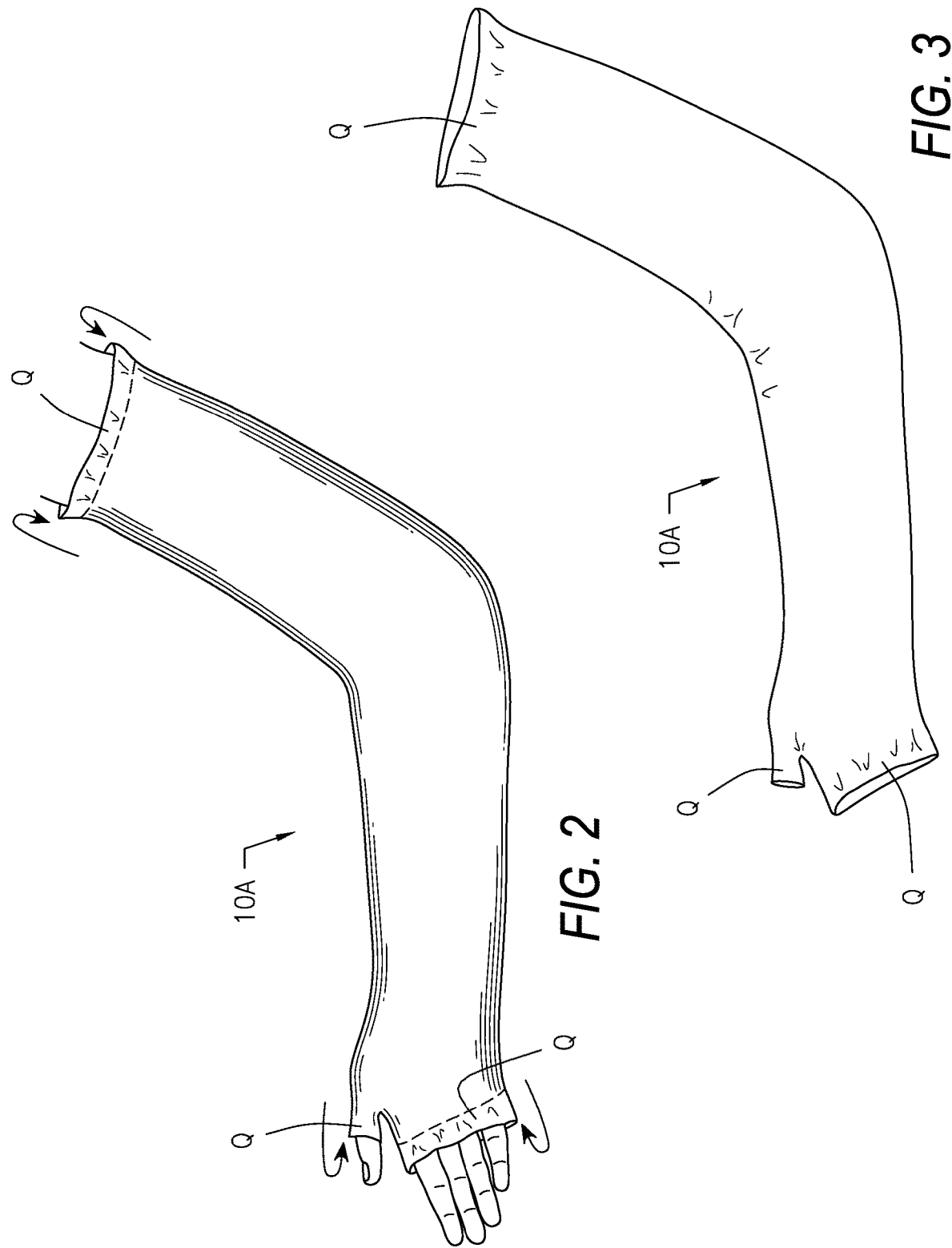

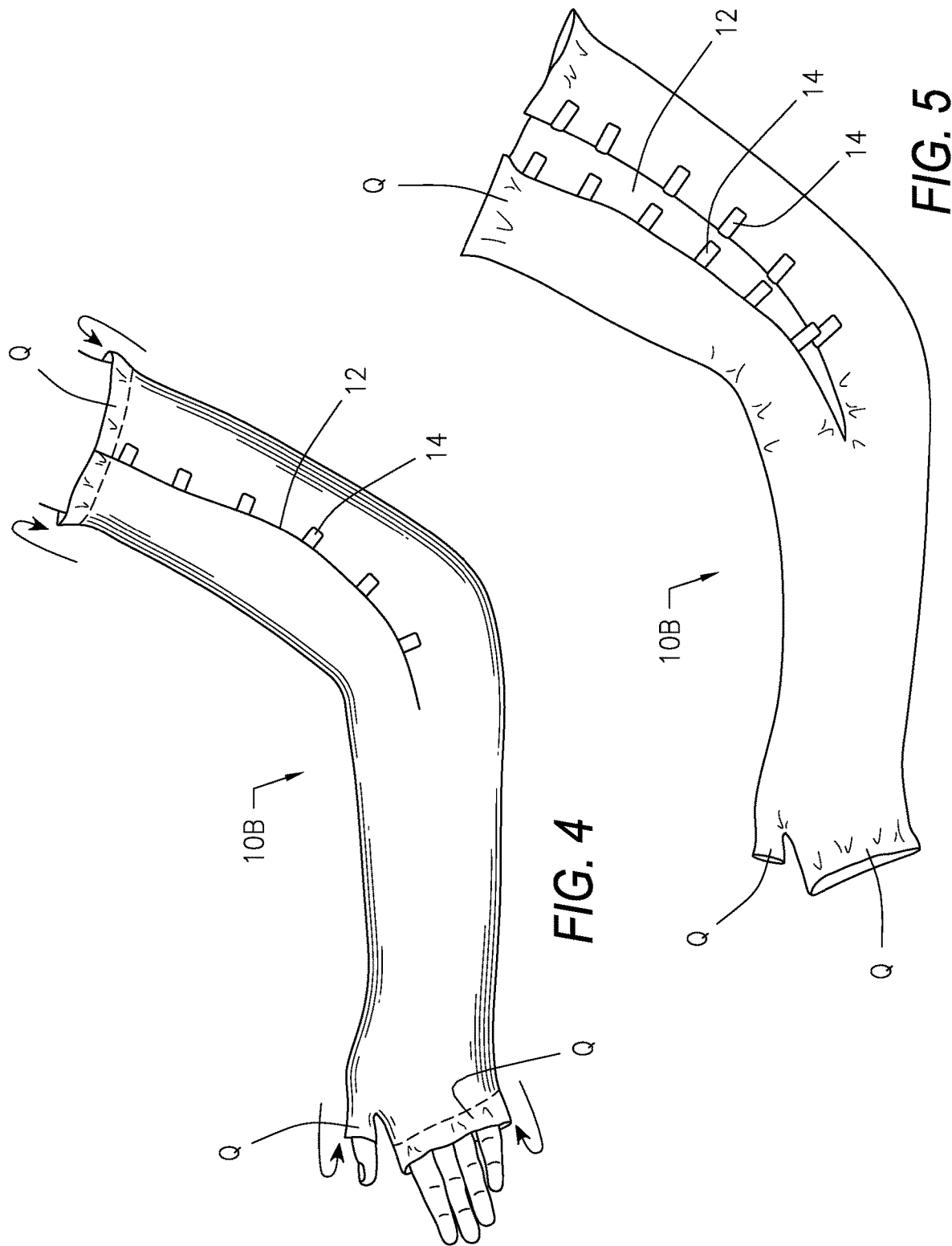

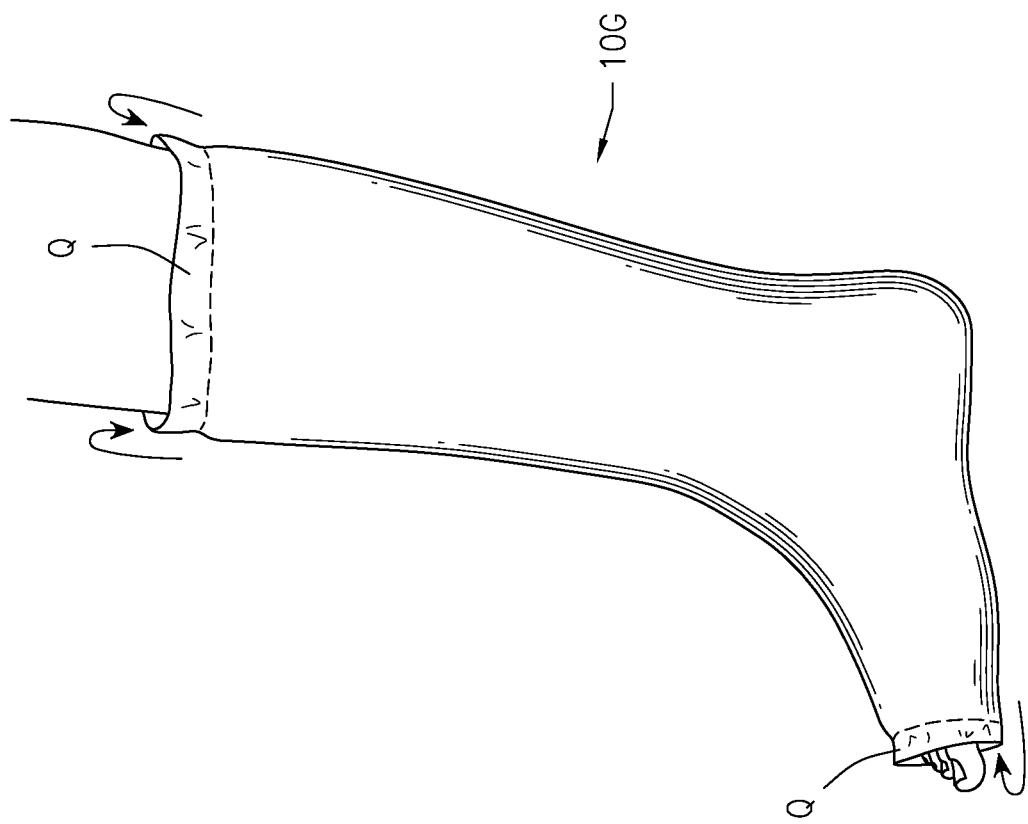

PROTECTIVE COVER FOR CAST

CROSS-REFERENCE TO RELATED APPLICATIONS

The present application claims priority to U.S. Provisional Application Ser. No. 62/333,444 filed on May 9, 2016 for Protective Cover for Cast.

BACKGROUND OF THE INVENTION

1. Field of the Invention

The present invention is a protective cover for use over a cast, splint or brace to prevent soiling of the cast, splint or brace from bodily fluids, excrement, etc. This cover is designed to remain on the cast, splint or brace until the cast, splint or brace is removed but has the versatility to be fully removed and replaced should the need arise. The protective cover is constructed of a material that is readily cleanable by wiping with a damp cloth, disinfecting wipe/solution or soap. Preferred material for construction of the cover include, but are not limited to nitrile, silicone rubber, and epichlorohydrin rubber.

2. Description of the Related Art

Because a cast, splint or brace must remain on a person's body for an extended period of time to allow the person's broken bones or body parts to heal, a cast, splint or brace will invariably be exposed to a variety of things that will soil it. Some of those things can cause the cast, splint or brace to become unsanitary, look bad, smell bad, and feel bad as the soiled surfaces can irritate the patient's skin.

Various covers have been proposed for covering a cast, splint or brace. Some of these are made of cloth or other types of material that are generally used for decorative purposes. These covers will become soiled and do not protect the cast, splint or brace from liquids and bodily fluids, such as for example urine.

Other covers completely cover the appendage so that the hand or foot is also covered along with the cast, splint or brace. These types of covers are generally used when the person is bathing or swimming and are not appropriate for wearing all the time, and they interfere with skin and neurovascular examination/inspection.

Still other covers are designed with elastic that can become constrictive and uncomfortable.

Some covers are designed only to prevent damage to furniture or other external objects with which the cast, splint or brace may come in contact. These covers do little to protect the cast, splint or brace from being soiled by bodily fluids.

Still other covers are simply designed to prevent irritation to the wearer at the edges of the cast, splint or brace so that the cast, splint or brace does not rub against the wearer's skin at the openings into the cast, splint or brace.

The present invention addresses the shortcomings of previous covers by providing a cast, splint or brace cover that is comfortable to the wearer so that it can remain on the cast, splint or brace until the cast, splint or brace is removed and also protects the cast, splint or brace from being soiled by bodily fluids, excrement, etc. The invention is made of material that can be cleaned by wiping with a damp cloth, or disinfecting wipe/solution or soap making it easily to maintain.

SUMMARY OF THE INVENTION

The present invention is a protective cover for use over a cast, splint or brace to prevent soiling of the cast, splint or brace from bodily fluids, excrement, etc. This cover is designed to remain on the cast, splint or brace until the cast, splint or brace is ready to be taken off. However, the cover has the versatility to be fully removed and replaced should the need arise. The protective cover is constructed of a material that is readily cleanable by wiping with a damp cloth. The material is soft and smooth to the skin so that it can remain next to the skin of the person wearing the cast, splint or brace for an extended period without causing any adverse reactions or skin irritation. The material is hypoallergenic and is not known to cause any adverse reactions.

The cover is in the shape of the cast, splint or brace with additional material provided at each of the cast, splint or brace openings so that the additional material can be tucked inside the cast, splint or brace to protect the cast, splint or brace from soiling. Depending on the shape of the cast, splint or brace over which the cover is to be fitted, the cover may optionally be provided with a slit in the material to facilitate fitting it onto the cast, splint or brace. The slit is provided with hook and loop fasteners or other suitable fastening means, such as but not limited to Velcro® tabs, on each side of the slit as a means of securing the slit together to fit the cover over the cast, splint or brace.

BRIEF DESCRIPTION OF THE DRAWINGS

FIG. 2 is a perspective view of a first alternate protective cover for a cast, splint or brace illustrated in use with a full arm cast.

FIG. 3 is a perspective view of the first alternate protective cover of FIG. 2 shown removed from the cast.

FIG. 4 is a perspective view of a second alternate protective cover with slit for a cast, splint or brace illustrated in use with a full arm cast allowing for a spreader/support bar. This view shows the fastening means closed.

FIG. 5 is a perspective view of the second alternate protective cover with slit of FIG. 4 shown removed from the cast. This view shows the fastening means open.

FIG. 15 is a side view of a seventh alternate protective cover for a lower leg and foot cast shown secured to the cast.

DETAILED DESCRIPTION OF THE PREFERRED EMBODIMENT

Figure 1:
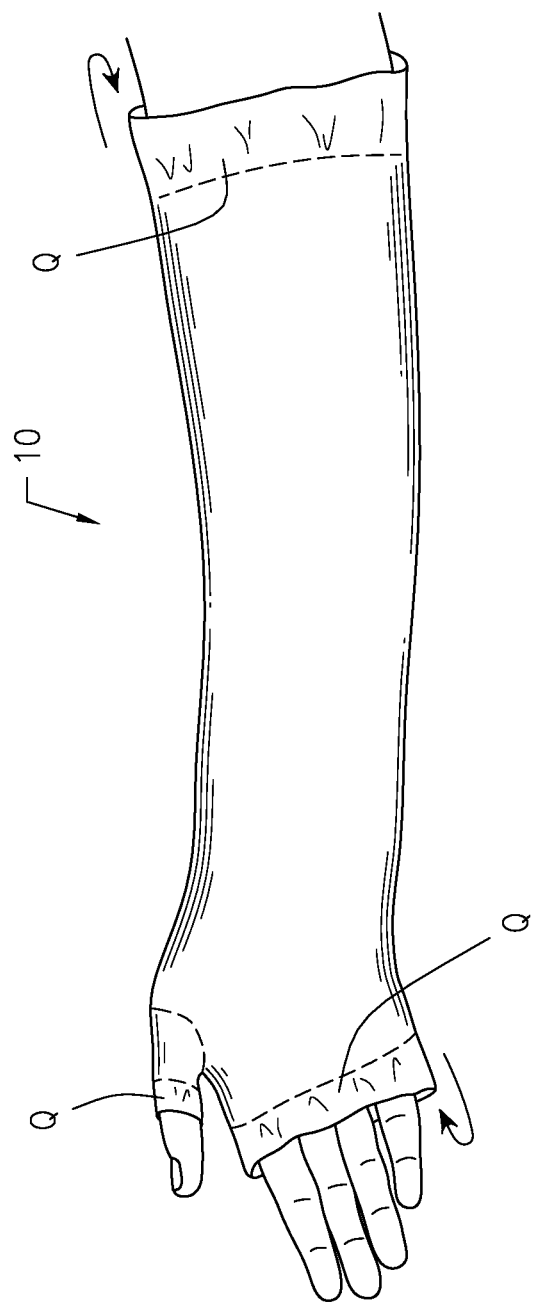
FIG. 1 is a perspective view of a protective cover for a cast, splint or brace that is constructed in accordance with a preferred embodiment of the present invention. The cover is illustrated in use with a partial arm cast.
Figure 6:
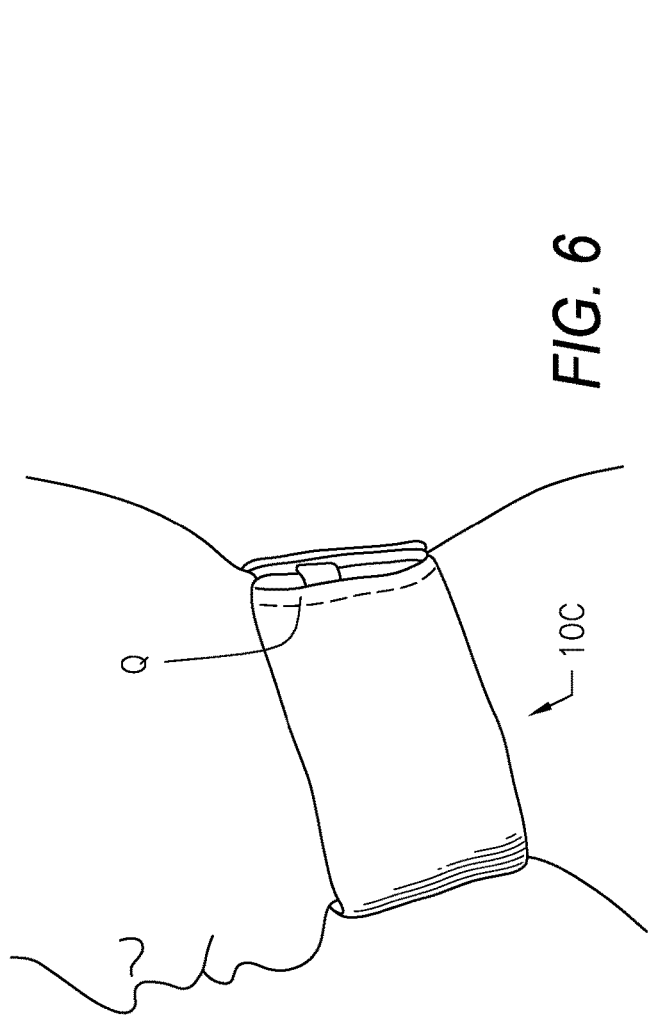
FIG. 6 is a perspective view of a third alternate protective cover for a cast illustrated in use with a collar.
Figure 7:
FIG. 7 is a perspective view of the third alternate protective cover of FIG. 6 shown removed from the collar.
Figure 10:
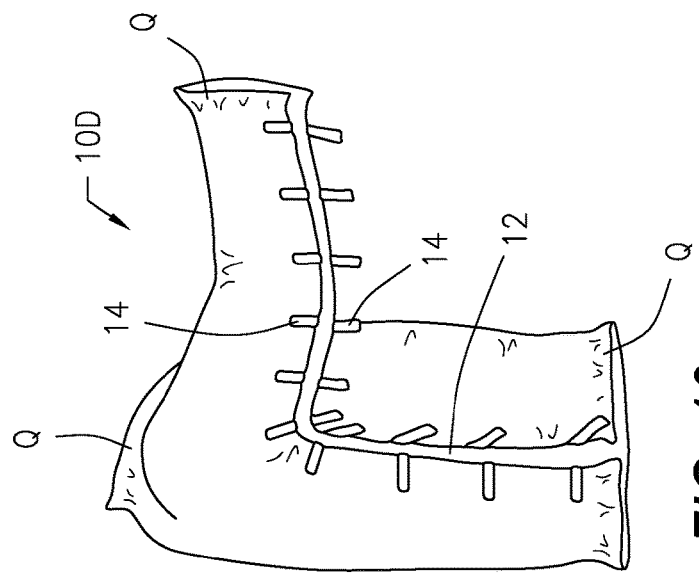
FIG. 10 is a side view of the fourth alternate protective cover of FIG. 8 shown removed from the cast. This view shows the fastening means open.
Figure 8:
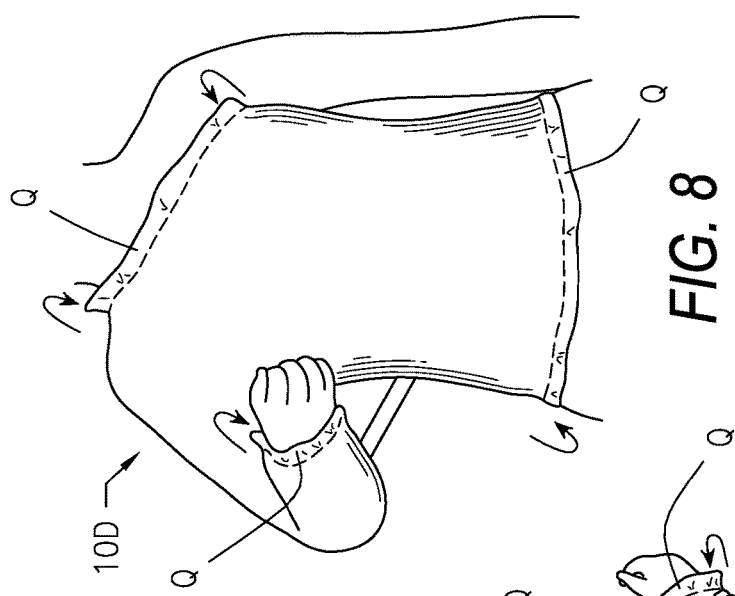
FIG. 8 is a front view of a fourth alternate protective cover with slit for a cast, splint or brace illustrated in use with a torso and arm cast allowing for a spreader/support bar.
Figure 9:
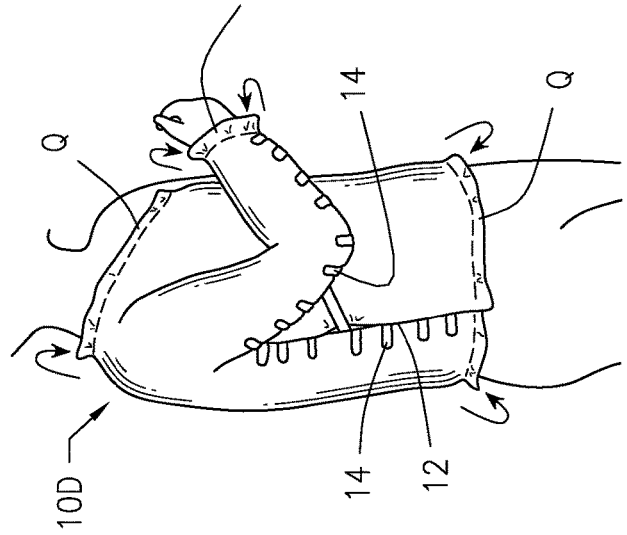
FIG. 9 is a side view of the fourth alternate protective cover of FIG. 8. This view shows the fastening means closed.
Figure 12:
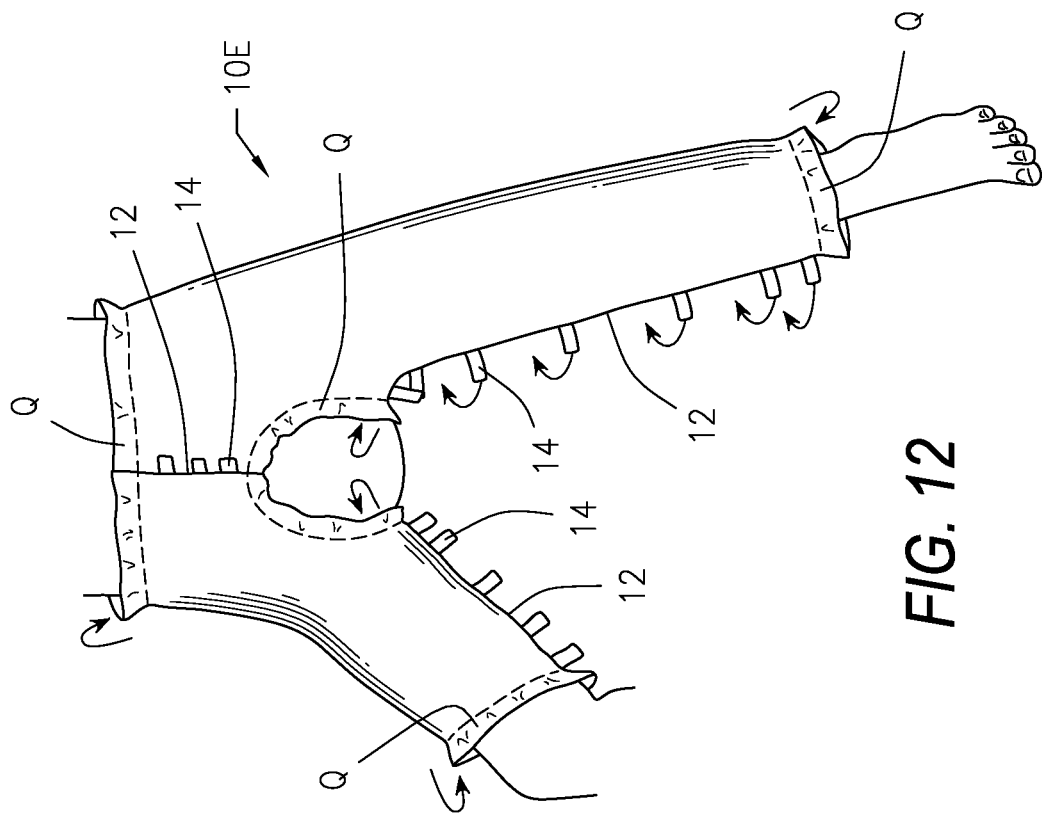
FIG. 12 is a front view of the fifth alternate protective cover of FIG. 11 shown being secured to a lower body, full leg and short leg cast.
Figure 11:
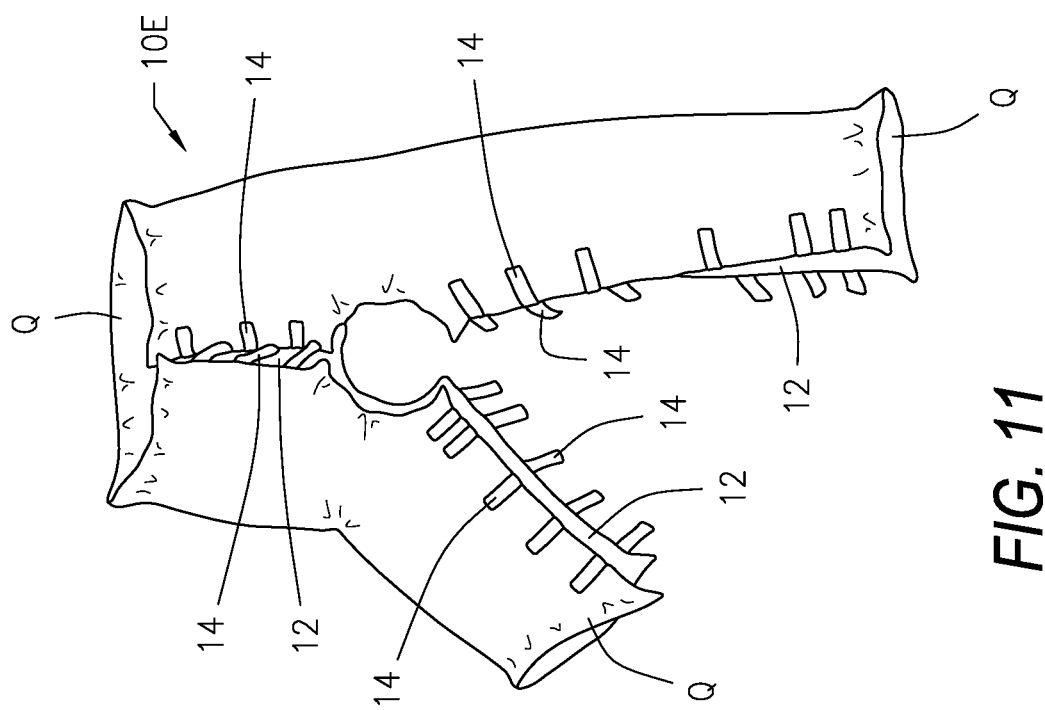
FIG. 11 is a front view of a fifth alternate protective cover with slits for a lower body, full leg and short leg cast. This fifth alternate protective cover is available with front fastening, back fastening or fastening on both front and back depending on need for toileting and diapering care and allowing for a spreader/support bar.
Figure 14:
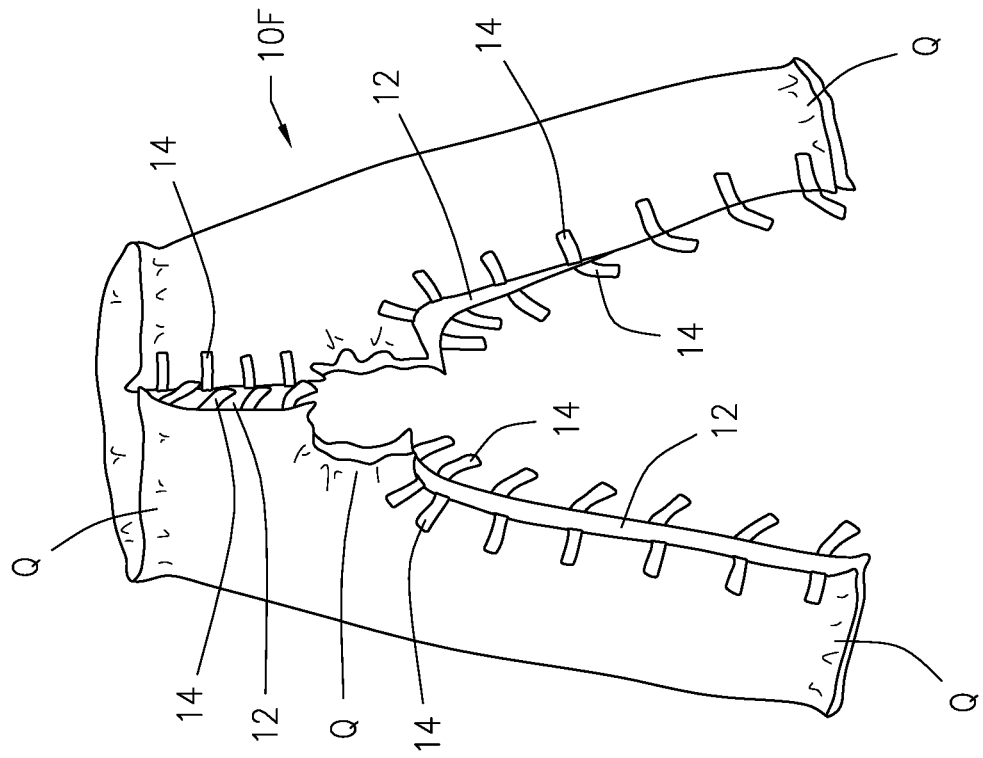
FIG. 14 is a front view of the sixth alternate protective cover of FIG. 13 shown removed from the cast.
Figure 13:
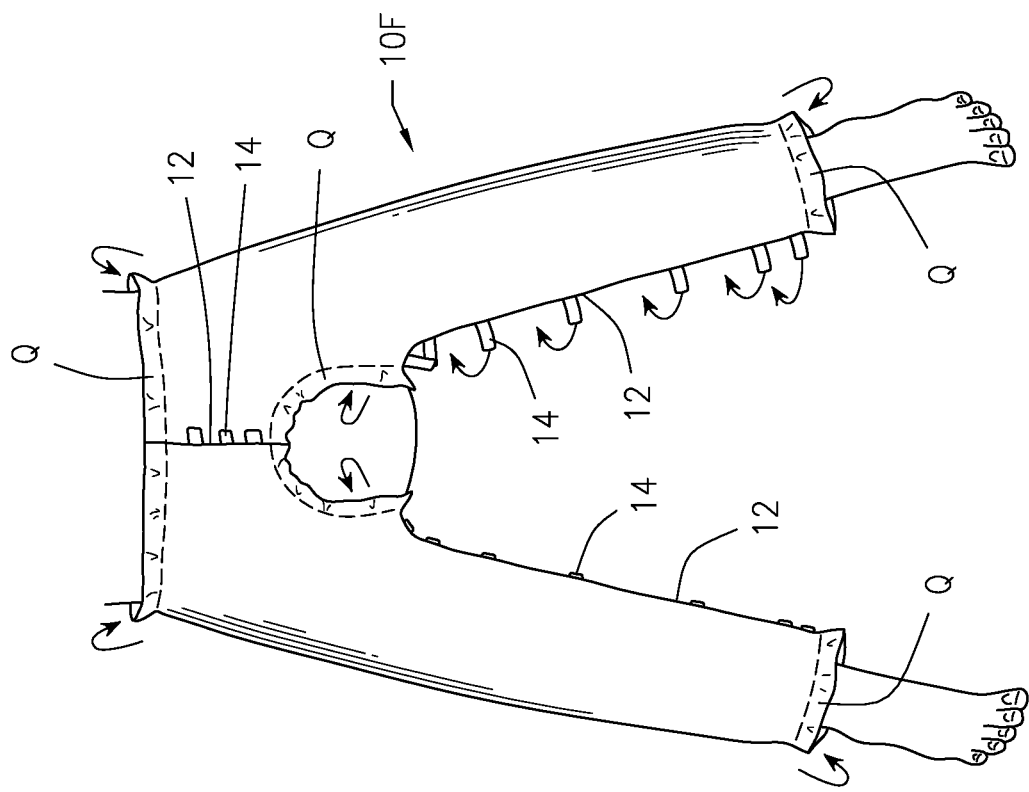
FIG. 13 is a front view of a sixth alternate protective cover with slits shown in use with a lower body and two full legs cast. This sixth alternate protective cover is available with front fastening, back fastening or fastening on both front and back depending on need for toileting and diapering care and allowing for a spreader/support bar.
Figure 17:
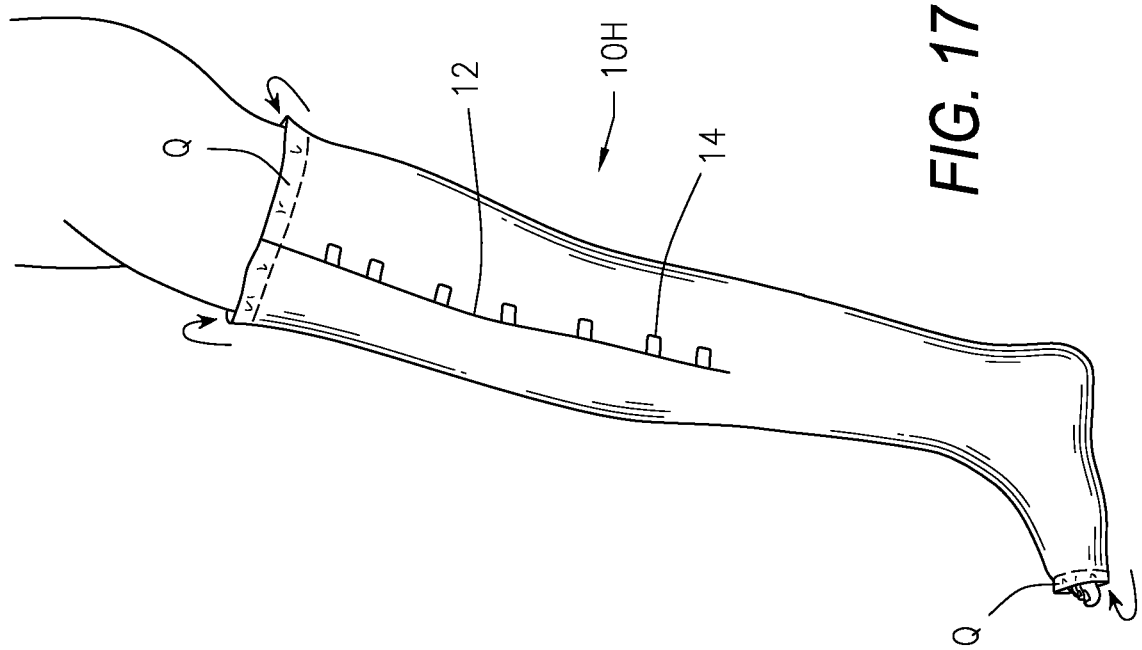
FIG. 17 is a side view of the eighth alternate protective cover of FIG. 16 shown secured to a cast.
Figure 16:
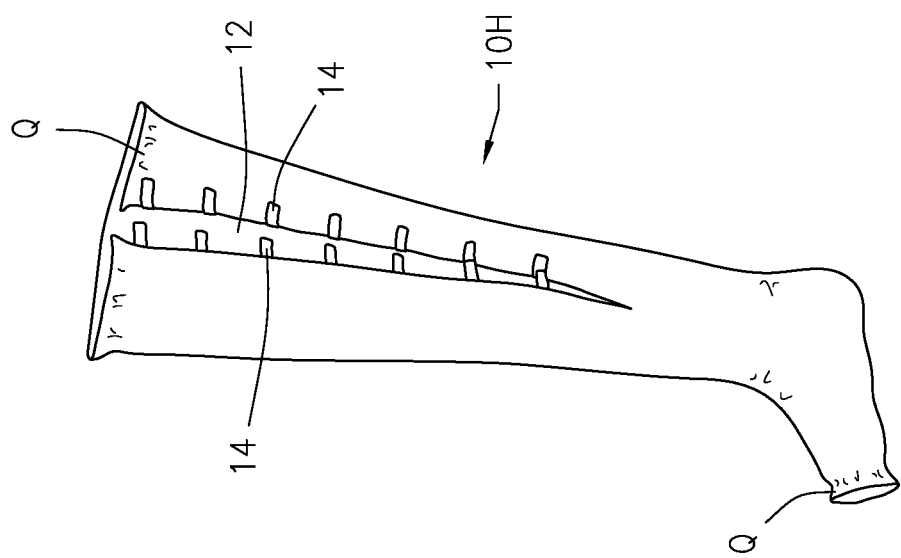
FIG. 16 is a side view of an eighth alternate protective cover with slit for a full leg cast. This either alternate protective cover can be worn on either leg with fasteners on inside or outside and allowing for a spreader/support bar.

Referring now to the drawings and initially to FIG. 1, there is illustrated a protective cover 10 for use over a cast or support collar to prevent soiling of the cast, splint or brace from bodily fluids, excrement, etc. This cover 10 is designed to remain on the cast, splint or brace and is not to be removed until the cast, splint or brace is ready to be taken off. However, the cover has the versatility to be fully removed should the need arise. The protective cover 10 is constructed of a material that is readily cleanable by wiping with a damp cloth or disinfecting wipe/solution or soap.

The material is soft and smooth to the skin so that it can remain next to the skin of the person wearing the cast, splint or brace for an extended period without causing any adverse reactions or skin irritation. The material is hypoallergenic and is not known to cause any adverse reactions. The preferred materials from which the cover 10 is made are nitrile, silicone rubber, or epichlorohydrin rubber.

As illustrated in FIGS. 1-17, the covers 10 and alternate covers 10A, 10B, 10C, etc. are each constructed in the shape of the cast, splint or brace for which they are designed and each is provided with additional material Q at each of the cast, splint or brace openings so that the additional material can be tucked inside the cast, splint or brace to protect the cast, splint or brace from soiling. As illustrated in FIGS. 4-5, 9-14, and 16, depending on the shape of the cast, splint or brace over which the covers or alternate covers 10, 10A, 10B, 10C, etc. are to be fitted, the covers or alternate covers 10, 10A, 10B, 10C, etc. may optionally be provided with one or more slits. The covers 10, 10A, 10B, 10C, etc. are available with front fastening, back fastening, side fastening or fastening on multiple locations depending on the need for toileting and diapering care and allowing for a spreader/support bar.

Slits 12 may optionally be provided in the covers 10, 10A, 10B, 10C, etc. to facilitate fitting them onto the cast, splint or brace. Each slit 12 is provided with hook and loop fasteners or Velcro® fasteners 14 or other suitable fastening means on each side of the slit 12 as a means of securing the slit 12 together to fit the covers 10, 10A, 10B, 10C, etc. over the cast, splint or brace. When thus fitted over a cast, splint or brace, the cover or alternate covers 10, 10A, 10B, 10C, etc. completely cover all exposed surfaces of the cast, splint or brace and a portion of the underside of the edge of the cast, splint or brace to protect the cast, splint or brace from soiling and to aide in contaminants from communicating with the underside of the cast, splint or brace and cast, splint or brace liner.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A protective cover for a cast, splint or brace having ends and a length, the cover comprising:
    a tube shaped cover having at least two openings, the tube shaped cover having a length being longer than the length of the cast, splint or brace over which it is to be inserted, and
    an extension of additional material (Q) extending from the tube shaped cover proximate each of the at least two openings of the tube shaped cover, characterized in that each said extension of additional material (Q) flares outwardly with respect to the opening of the tube shaped cover from which it extends and can be tucked into the corresponding end of the cast, splint or brace to cover the corresponding end of the cast, splint or brace.

2. A protective cover according to claim 1 wherein the tube shaped cover has at least three openings and wherein an extension of additional material (Q) extends from the tube shaped tube shaped cover proximate each of the at least three openings of the tube shaped cover, characterized in that each said extension of additional material (Q) flares outwardly with respect to the opening of the tube shaped cover from which it extends and can be tucked into the corresponding end of the cast, splint or brace to cover the corresponding end of the cast, splint or brace.

3. A protective cover according to claim 2 further comprising:
    the tube shaped cover provided with at least one slit that extends from one opening of the tube shaped cover to another opening of the tube shaped cover, and fasteners provided associated with each slit for removably securing the slit together.

4. A protective cover according to claim 3 wherein cover has a front and a back and the cover comprises front fastening, back fastening or fastening on both front and back.

5. A protective cover according to claim 2 wherein the tube shaped cover comprises a main body and at least one limb extension extending from the main body so that the cover may be worn over a cast, splint or brace that is installed partially or fully on an abdomen and on a limb of a wearer, wherein the main body of the cover is adapted to be worn partially or fully over a cast, splint or brace installed partially or fully on the abdomen of the wearer and wherein the at least one limb extension extending from the main body is adapted to be worn partially or fully over a limb of the wearer.

6. A protective cover according to claim 5 wherein the cover forms an aperture adapted to permit a wearer to evacuate while wearing the cover.

7. A protective cover according to claim 1 further comprising:
    the tube shaped cover provided with at least one slit that extends from one opening of the tube shaped cover to another opening of the tube shaped cover, and fasteners provided associated with each slit for removably securing the slit together.

8. A protective cover according to claim 1 further comprising:
the tube shaped cover provided with at least one slit that extends from one opening of the tube shaped cover part way to another opening of the tube shaped cover, and fasteners provided associated with each slit for removably securing the slit together.

9. A protective cover according to claim 1 wherein the cover is made from a material selected from the group consisting of nitrile, silicone rubber or epichlorohydrin rubber.

10. A protective cover according to claim 1 wherein the extension of material forms a flange shape.

11. A protective cover according to claim 1 wherein the extension of material forms a ruffle shape.

12. A protective cover according to claim 1, wherein the cover is adapted to be worn over a cast, splint or brace installed on an arm, leg, foot, neck, or abdomen of a patient, or a combination of the foregoing.

13. A protective cover according to claim 1 wherein the cover is adapted to accommodate toileting and diapering care or a spreader or support bar installed on the cast, splint or brace.

14. A method of protecting a cast, splint or brace having ends and a length, the method comprising the steps of:
providing a tube shaped cover, wherein:
the tube shaped cover has at least two openings and a length being longer than the length of the cast, splint or brace;
the tube shaped cover has an extension of additional material (Q) extending from the tube shaped cover proximate each of the at least two openings of the tube shaped cover, characterized in that each said extension of additional material (Q) flares outwardly with respect to the opening of the tube shaped cover from which it extends;
installing the tube shaped cover over the cast, splint or brace; and
tucking the extension of additional material (Q) into the corresponding end of the cast, splint or brace to cover the corresponding end of the cast, splint or brace.

15. The method of claim 14 further comprising the steps of:
providing the tube shaped cover with at least one slit that extends from one of the openings of the tube shaped cover to another one of the openings of the tube shaper cover;
providing fasteners associated with each slit; and
removably securing the slit together.

16. The method of claim 14 further comprising the steps of:
providing the tube shaped cover with at least one slit that partially extends from one of the openings of the tube shaped cover to another one of the openings of the tube shaper cover;
providing fasteners associated with each slit; and
removably securing the slit together.

17. The method of claim 14 further comprising the step of removing the cover from the cast, splint or brace.

* * * * *